United States Patent [19]
Schwierzke et al.

[11] Patent Number: 5,506,507
[45] Date of Patent: Apr. 9, 1996

[54] APPARATUS FOR MEASURING IONS IN A CLEAN ROOM GAS FLOW USING A SPHERICAL ELECTRODE

[75] Inventors: Jörg Schwierzke; Hans-Henrich Stiehl; Joachim Lohr, all of Berlin, Germany

[73] Assignee: Sorbios Verfahrenstechnische Geräte und Systeme GmbH, Germany

[21] Appl. No.: 122,931

[22] Filed: Sep. 17, 1993

[30]     Foreign Application Priority Data

Sep. 18, 1992 [DE] Germany .................... 42 31 905.6

[51] Int. Cl.⁶ ........................................... G01N 27/62
[52] U.S. Cl. ................................. 324/464; 324/459
[58] Field of Search ........................ 324/464, 459, 324/465, 71.1, 72; 361/213, 229, 230, 231, 232

[56]              References Cited

U.S. PATENT DOCUMENTS

| | | | |
|---|---|---|---|
| 3,248,644 | 4/1966 | Streib et al. | 324/464 |
| 3,359,796 | 12/1967 | Dimick | 324/464 |
| 4,435,681 | 3/1984 | Masuda et al. | 324/464 |

*Primary Examiner*—Walter E. Snow
*Attorney, Agent, or Firm*—Young & Basile

[57]              ABSTRACT

An apparatus for measuring ions in a gas which has a sensor around which the gas flows, the ions giving off their charge and giving rise to a current. The sensor is constructed as an electrode with a flow-favorable shape, such as a sphere. A fixed voltage is impressed on the electrode and the current produced at the electrode is measured, evaluated in a circuit and constitutes a measure for the ion count.

8 Claims, 1 Drawing Sheet

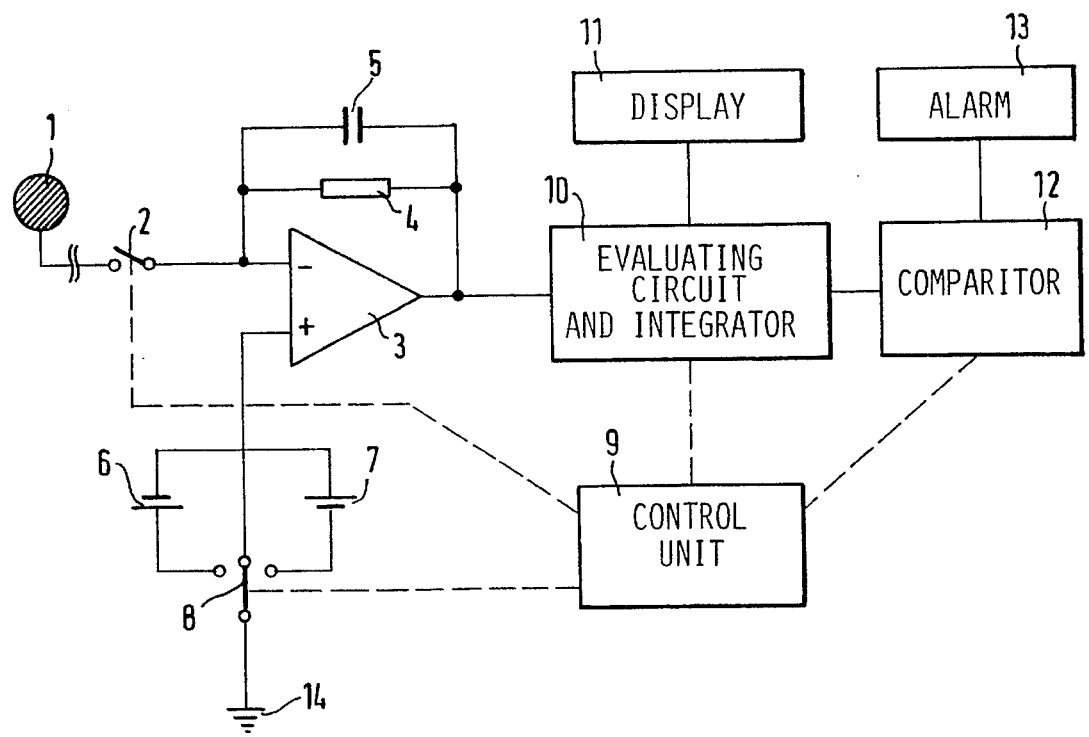

APPARATUS FOR MEASURING IONS IN A CLEAN ROOM GAS FLOW USING A SPHERICAL ELECTRODE

BACKGROUND OF THE INVENTION

1. Field of the Invention

The invention relates to an apparatus for measuring ions in a gas.

2. Description of the Art

The prior art discloses an apparatus for measuring ions in a gas in the form of an ion counter in which the sensor is constituted by a large and usually cylindrical capacitor with a gaseous dielectric. The gas in which the ion count is to be determined is passed through the capacitor. A high voltage is applied to the capacitor plates and the positive ions are deflected to the negatively charged plates and the negative ions to the positively charged plates where they give off their charge. The resulting current can be measured and constitutes a measure of the ion count.

In addition, an apparatus is known which makes it possible to measure the ion balance in that the gas flows past an electrode and the charge excess of one polarity on the electrode gives rise to a correspondingly directed measurable current. As the ion mobility is polarity-dependent, there is a charge equilibrium (ion balance) on the electrode in the case of somewhat differing ion densities in the gas.

Based on this prior art, the problem of the invention is to provide an apparatus for measuring ions in a gas which is small, takes up little space, gives rise to a minimum disturbance to the gas flow and is independent of the direction and speed of the flow, the sensor being connectable via a long cable to the processing electronics.

SUMMARY OF THE INVENTION

Due to the fact that the sensor is constituted by an electrode, which is favorable from a flow standpoint and is preferably spherical and very small, e.g. <20 mm, the gas flow is hardly disturbed and the charge of the ions is recorded in an almost direction-independent manner. The voltage of this electrode relative to earth potential or reference potential is impressed by the electric circuit. Thus, the sensor can be connected by means of a long cable because the cable capacitance does not have to be charge reversed by the measuring signal. The impressed voltages are very small, e.g. <30 V, so that together with the very small capacitance of the sensor with respect to the environment the influenced voltage by the sensor is very small.

The invention includes features which permit advantageous further developments and improvements. Due to the fact that cyclically different voltages are impressed, it is possible to measure the number of positive ions (negative voltage), the number of negative ions (positive voltage) and the ion balance (zero voltage), whereby in all three cases the current which flows to the sphere through the ion charge delivery is determined.

Preferably the current is measured with a current-voltage converter having a feedback operational amplifier which simultaneously ensures that the sphere potential remains constant. By filtering the current with a lower critical frequency filter, e.g. 30 MHz, it is possible to suppress interference such as is caused by periodic alternating current fields or by briefly influenced offset currents.

In a preferred embodiment the a.c. components are largely eliminated by the up-slope integration of the current over a given time period. The measured values can be compared with the given threshold values so that a signal can be emitted on passing above or below such values.

By means of the present invention, for example the ion density in a clean room for the manufacture of integrated circuits or the like and through which an air flow is passed, can be monitored.

DESCRIPTION OF THE PREFERRED EMBODIMENT

An embodiment of the invention is described in greater detail hereinafter relative to the drawing showing the circuitry of the apparatus for the measurement of ions according to the present invention.

In the drawing reference number 1 depicts a sensor, which is constructed as a spherical electrode and which has a diameter of preferably <20 mm. By means of a switch 2, which is controlled by a control unit 9, the electrode 1 is connected to the inverting input of an operational amplifier 3, whereby the connection can be a cable which is several meters long. The operational amplifier 3 is applied with negative feedback from its output, across a resistor 4 to the inverting input, so that the operational amplifier 3 functions as a current-voltage converter. The operational amplifier 3 is provided with a.c. negative feedback through the capacitor 5 which is parallel to the resistor 4.

The non-inverting input of the operational amplifier 3 is connected to a reference potential 14, a negative voltage source 6 or a positive voltage source 7 via a switch 8, which is also controlled by the control unit 9. The output of the operational amplifier 3 is connected to an evaluating circuit 10, which is in turn connected to a display 11, a comparator 12 and an alarm unit 13. The evaluating circuit 10 and the comparator 12 are also controlled by the control unit 9.

In clean rooms, the electric charges in the air are neutralized by air ionization. For this purpose it is necessary to have a continuous monitoring of, e.g., the ion density, which is performed with the apparatus according to the invention. For measuring the ion count in the gas, e.g., air flowing past the electrode 1, the control unit 9 controls the switch 8 on the positive or negative voltage source 6,7. The positive or negative voltage is applied to the non-inverting input of the operational amplifier 3 and the voltage at the electrode 1 is set to this positive or negative voltage. The ions flowing past the spherical electrode 1 deliver their charge in an almost direction-independent manner to the electrode 1 so that an evaluatable current flows. If the electrode 1 is a sphere, then according to Rieck, the current absorbed by the sphere can be determined as:

$$I^+ = 4\pi e\, n^+ k^+ C\, U^-,$$

in which R is the sphere radius, e the elementary charge, n the number of ions, k the ion mobility, C the capacitance of the sphere with respect to the environment and U the voltage of the sphere related to earth potential. For the current which is produced by the negative ions the sign must be reversed. As can be gathered from the above formula, the current is independent of the gas velocity. The current from the sensor or electrode 1 flowing across the closed switch 2 is compensated by the operational amplifier 3 functioning as a current-voltage converter and across the resistor 4, so that the output voltage is a product of the resistor 4 and the sensor current. The voltage at the electrode 1 is always regulated, independently of the input current, to the value at the non-inverting input of the operational amplifier 3. As a result of the negative feedback of the capacitor 5 the current-voltage-converter receives a low-pass characteristic so that interference induced on the electrode 1 and which could be caused, for example, by an ion generator is suppressed. Such spurious electrical signals are coupled in to the interference source as interference current via the low sensor capacitance. Spurious a.c. voltages appear at the output of the operational amplifier 3 attenuated by the ratio of the sensor capacitance to the interference source/negative feedback capacitance 5.

In the evaluating circuit 10 the voltage supplied by the operational amplifier 3 is optionally stored and evaluated in accordance with the Rieck formula, so that the number of ions present can be determined, this number being displayed on the display II.

For the ion balance measurement the control unit 9 controls the switch 8 in such a way that there is earth potential 14 at the non-inverting input of the operational amplifier 3 so that the voltage is zero. Preferably the switch 8 is controlled in such a way that in cyclic succession the different voltages, namely the positive, negative and zero voltages are impressed, so that successively the measurement of the positive ion count, negative ion count and ion balance takes place.

In order to avoid errors due to the drift of offset currents and voltages, the control unit 9 controls the switch 2 in regular intervals in the opened state, after which a measurement can be performed without the current supplied by the electrode 1. This measured value is stored in the evaluating circuit 10 and is deducted during all of the following measurements. The comparing circuit 12 stores threshold voltages for the ion counts and compares the measured values supplied by the evaluating circuit 10 with the threshold values. If the measured values exceed or drop below the threshold values, the comparing circuit 12 supplies a signal to the alarm circuit 13 and triggers an optical or acoustic alarm. The evaluating circuit 10 stores the measured values so that they can be individually or collectively displayed on the display 11, which can, for example, be connected via a data line or can be a personal computer.

In the above embodiment, a fixed voltage based on earth potential is cyclically impressed on the electrode I. In another embodiment the impressing of a voltage on the electrode I, based on the earth potential, can also take place in that the non-inverting input of the operational amplifier is applied to circuit earth and for this purpose there is a modification to the circuit earth on the complete layout based on the earth potential. If the electrode has a voltage with respect to the earth potential, then from the gas flow the ions of opposite polarity will deliver their charge to the electrode 1. The current which is then to be measured is directly proportional to the number of the corresponding ions.

In the described embodiment, interference by periodic a.c. fields or briefly influenced offset currents are avoided by filtering the current with a low critical frequency filter. In another embodiment the current is up-slope integrated in an integrator over a given period and the ion count is determined as a function of the integration time using the Rieck formula, the integrator being simultaneously reset. The level of the integrated signal is a measure of the d.c. component to be measured, while the a.c. components in the signal are largely suppressed.

A sphere has been used as the electrode 1 in the above description. However, other flow favorable shapes are conceivable (streamline, ellipsoid, etc.).

We claim:

1. An apparatus for measuring ions in a gas flowing in a substantially field free environment using a sensor around which the gas flows, the ions giving off their charge, and with an electrical circuit for evaluating the current caused by the charges, characterized in that the sensor is constructed as an electrode with a flow-favorable shape with a fixed voltage of changing polarity impressed on the electrode, and that the current is filtered with a low critical frequency filter.

2. The apparatus according to claim 1, characterized in that the electrode is spherical.

3. The apparatus according to claim 1, characterized in that a negative voltage is impressed on the electrode for measuring the number of positive ions, a positive voltage is impressed on the electrode for measuring the number of negative ions and a zero voltage relative to the reference potential is impressed on the electrode for measuring the ion balance.

4. The apparatus according to claim 1, characterized in that the electric circuit has a current-voltage converter.

5. The apparatus according to claim 3, characterized in that a switch controlled by a control unit is provided and by means of said switch and in a cyclic manner the different voltages are impressed on the electrode.

6. The apparatus according to claim 4, characterized in that the current-voltage converter is constructed as an operational amplifier with a resistor in a negative feedback branch.

7. The apparatus according to claim 1, characterized in that the ion count is determined by the electric circuit for evaluating the current caused by the charges and that a threshold value-storing comparing circuit is provided which compares the measured ion counts with the threshold values.

8. The apparatus according to claim 1, characterized in that an integrator for the up-slope integration of the current supplied by the electrode is provided and is in each case reset after fixed time intervals.

* * * * *